US005513655A

United States Patent [19]

Peimer et al.

[11] Patent Number: 5,513,655
[45] Date of Patent: May 7, 1996

[54] SURGICAL DRAPE FOR SURGERY ON AN EXTERMITY

[76] Inventors: Clayton A Peimer, 651 Lebrun Rd., Amherst, N.Y. 14226; Susan M. Bohn, 1035 Beach Rd. Apt. D-12, Cheektowaga, N.Y. 14225

[21] Appl. No.: 348,573

[22] Filed: Dec. 2, 1994

Related U.S. Application Data

[63] Continuation of Ser. No. 248,411, May 24, 1994, Pat. No. 5,383,476.
[51] Int. Cl.⁶ .......................... A61B 19/00; A61B 19/08
[52] U.S. Cl. ...................... 128/849; 128/852; 128/853
[58] Field of Search ........................ 128/849–856

[56] References Cited

U.S. PATENT DOCUMENTS

| 4,569,341 | 2/1986 | Morris | 128/853 |
| 4,570,628 | 2/1986 | Neal | 128/853 |
| 4,586,498 | 5/1986 | Morris | 128/853 |
| 4,807,644 | 2/1989 | Sandhaus | 128/853 |
| 4,896,465 | 1/1990 | Rhodes | 128/849 |
| 4,974,604 | 12/1990 | Morris | 128/853 |
| 5,002,070 | 3/1991 | Taylor | 128/853 |
| 5,010,899 | 4/1991 | Thompson | 128/849 |
| 5,080,108 | 1/1992 | Roth | 128/849 |
| 5,383,476 | 1/1995 | Peimer | 128/853 |

Primary Examiner—Michael A. Brown
Attorney, Agent, or Firm—Phillips, Lytle, Hitchcock, Blaine & Huber

[57] ABSTRACT

The present invention is a surgical drape 10 specifically designed for surgery on extremities (e.g. arm, hand, leg, foot). The drape 10 comprises a base sheet 11, a work surface 14, a dam 21 having an adjustable opening 22 and cord stays 25–32. The patient 18 lies under the drape while a subject extremity 23 is placed through the adjustable opening. The dam is made of an elastomeric material which forms a tight engagement around the subject extremity. The work area completely surrounds the dam and is substantially stronger than the base sheet to reduce accidental tearing and prevent instruments from slipping off from the drape. The work area extends a substantial distance around the dam to provide adequate protection from accidentally tearing the drape when surgery is conducted near the dam. The cord stays prevent cords from interfering with surgery or becoming contaminated as a result of falling to the operating room floor.

4 Claims, 3 Drawing Sheets

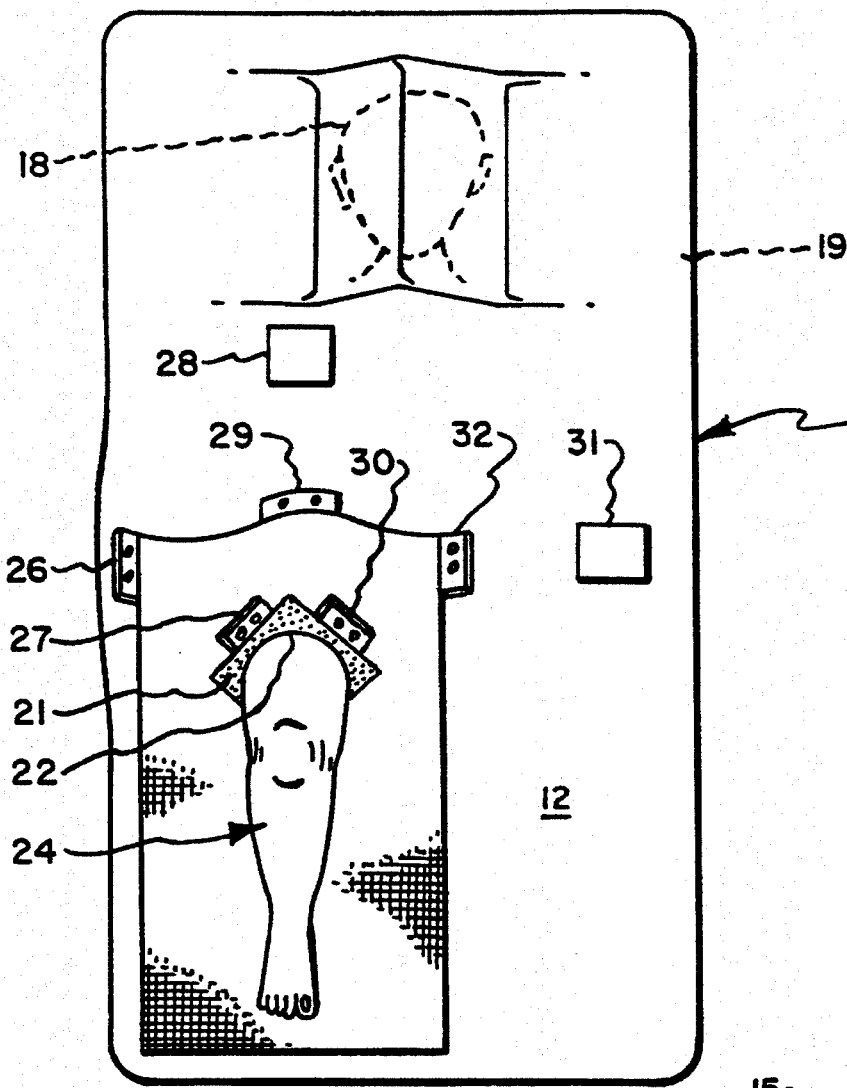
Fig. 3.
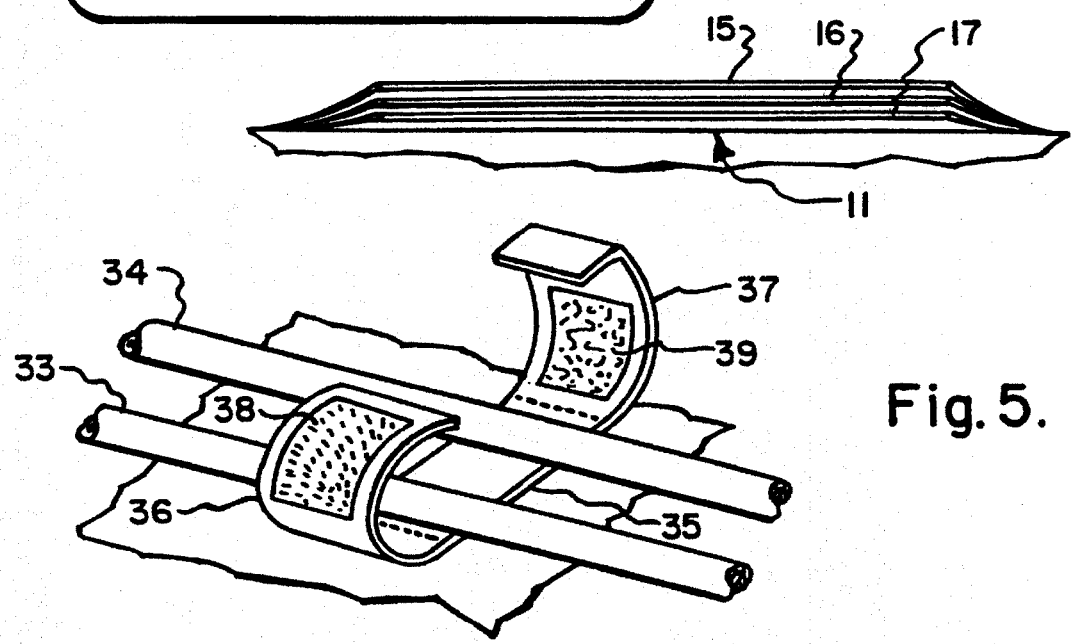
Fig. 4.
Fig. 5.

SURGICAL DRAPE FOR SURGERY ON AN EXTERMITY

This application is a continuation of Ser. No. 08/248,411, filed May 24, 1994, now U.S. Pat. No. 5,383,476.

TECHNICAL FIELD

The present invention relates generally to drapes suitable for covering a patient during surgery and more particularly, to a drape adaptable for use in lower or upper extremity surgery.

BACKGROUND OF THE INVENTION

Drapes for covering patients during surgery are well-known. These drapes form a sterile environment around the patient and a sterile work area for the surgical team. The sterile environment is maintained until the drape is breached.

As surgery has become more specialized, drapes adapted for specific surgeries have been developed. Extremity surgery (e.g., arm, hand, leg, foot) is one such specialty. Many attempts have been made in the prior art to create an extremity drape for universal application; i.e., a drape for use with any extremity of a patient regardless of age or size. Past attempts to design a universal extremity drape generally incorporated three modifications to the general surgical drape: first, an overall T-shape; second, inclusion of a rubber dam having an opening for the extremity to pass through; and third, reinforcing the drape in the area where the extremity lies during surgery.

The T-shape allows for surgery on an arm in its natural out-stretched position; i.e., perpendicular to the body. Integration of a rubber dam having an opening allows the body to remain covered by the drape while the extremity is placed through the opening in the rubber dam. The elastomeric qualities of the rubber dam tightly engage the extremity, thus maintaining the sterile environment under the drape. Reinforcing the drape reduces accidental tearing. A tear in the drape may breach the sterile surgical environment from, for example, improper instrument handling.

Nevertheless, extremity drapes in the prior art do not solve certain specific problems. In many instances prior art drapes are not large enough to cover a patient's entire body, and the surgical team ends up covering the patient with two or more drapes. Second, the dam opening in the prior art is often too large to tightly engage the extremities of a child. Loose engagement provides a path for easy transmission of infection to the patient. Third, prior art drapes do not provide a large enough reinforcement area adjacent to the dam to prevent accidental tearing of the drape when surgery is conducted near the dam. Finally, the absence of any structure integrated with the drape to hold cords immobile during surgery forces the surgical team to immobilize cords using methods which are likely to tear the drape, and thereby breaching the sterile surgical environment.

The present invention solves each of these four problems. First, a larger drape, having a specific shape, is contemplated to completely cover any size patient from an infant to a full-size adult. Second, the invention contemplates an opening through the dam small enough to tightly engage even the extremities of an infant. Third, the present invention provides a larger reinforced work area around the dam, reducing the possibility of accidental tearing of the drape while operating near the dam. Finally, the invention integrates unique cord stays to the drape allowing the surgical team to immobilize cords without increasing the risk of tearing the drape.

DISCLOSURE OF THE INVENTION

The present invention, (e.g., 10) is a universal drape specifically for use in extremity surgery. In particular, the preferred embodiment of the drape includes a base sheet (e.g., 11), a longitudinal work surface (e.g., 14), a dam (e.g., 21), and cords stays (e.g., 25–32).

The base sheet is generally T-shaped having a main area (e.g., 12) and an extension area (e.g., 13). The work surface is positioned on the base sheet, partially on the main area and partially on the extension area. The work surface is multi-layered, each layer performing a different task. The upper layer (e.g., 15) reduces sliding of instruments placed on the work surface and is more tear resistant than the base sheet. The middle layer (e.g., 16) is an absorbent material impregnated with an antimicrobial to reduce the infectious potential of liquids spilled on the work surface. The bottom layer (e.g., 17) is liquid impermeable, preventing liquids (e.g., blood, joint fluid, tissue irrigants) from seeping or leaking through the work surface into the base sheet.

In use, a patient (e.g., 18) lies on a surgical table (e.g., 19) under the main area. The subject extremity (e.g., 23) is placed through an adjustable opening (e.g., 22) defined by an elastomeric dam (e.g., 21) integrated with the drape. The subject extremity completely rests on the work surface.

The dam's elastomeric attributes ensure the dam tightly engages the subject extremity where it breaches the drape. This tight engagement reduces the possibility of contamination reaching the patient through the adjustable opening.

The longest distance across the dam is generally parallel with the longitudinal axis of the work surface. This allows the physician greater access to joints such as the hip and shoulder without sacrificing the benefits provided by the drape.

To provide adequate protection from accidents and unexpected movement when surgery is performed near the dam, the work surface extends well above the dam onto the main area.

Cord stays are positioned on the edge of the dam, the edge of the work surface and on the main area. Each cord stay is capable of holding at least one cord (e.g., 33) preventing a portion of the cord from interfering with surgery. The invention provides a single cord will be held by more than one cord stay, thus securing a longer length of cord from interfering at the site of surgery.

Thus, the primary object of the invention is to provide a universal drape for extremity surgery, adaptable for use on all sizes of extremities and patients.

Still another object of the invention is to provide a universal drape for extremity surgery having an adequate size non-skid, tear resistant surface on which surgery may safely be performed, including surgery adjacent the dam.

Still another object of the invention is to provide a universal drape for extremity surgery having an adjustable opening capable of tightly engaging any size extremity.

Still another object of the invention is to provide a universal drape for extremity surgery having cord stays capable of immobilizing cords at a distance from the site of surgery and further preventing the cords from moving and possibly becoming contaminated.

These and other objects of the invention will become apparent from the foregoing and ongoing written specification, the drawing figures and claims that follow.

BRIEF DESCRIPTION OF THE DRAWINGS

FIG. 3 is a top plan view of the drape as used during leg/foot surgery.

FIG. 4 is a cross section along line 4—4 in FIG. 1.

FIG. 5 is a perspective view of a first cord stay.

MODE(S) OF CARRYING OUT THE INVENTION

Figure 1:
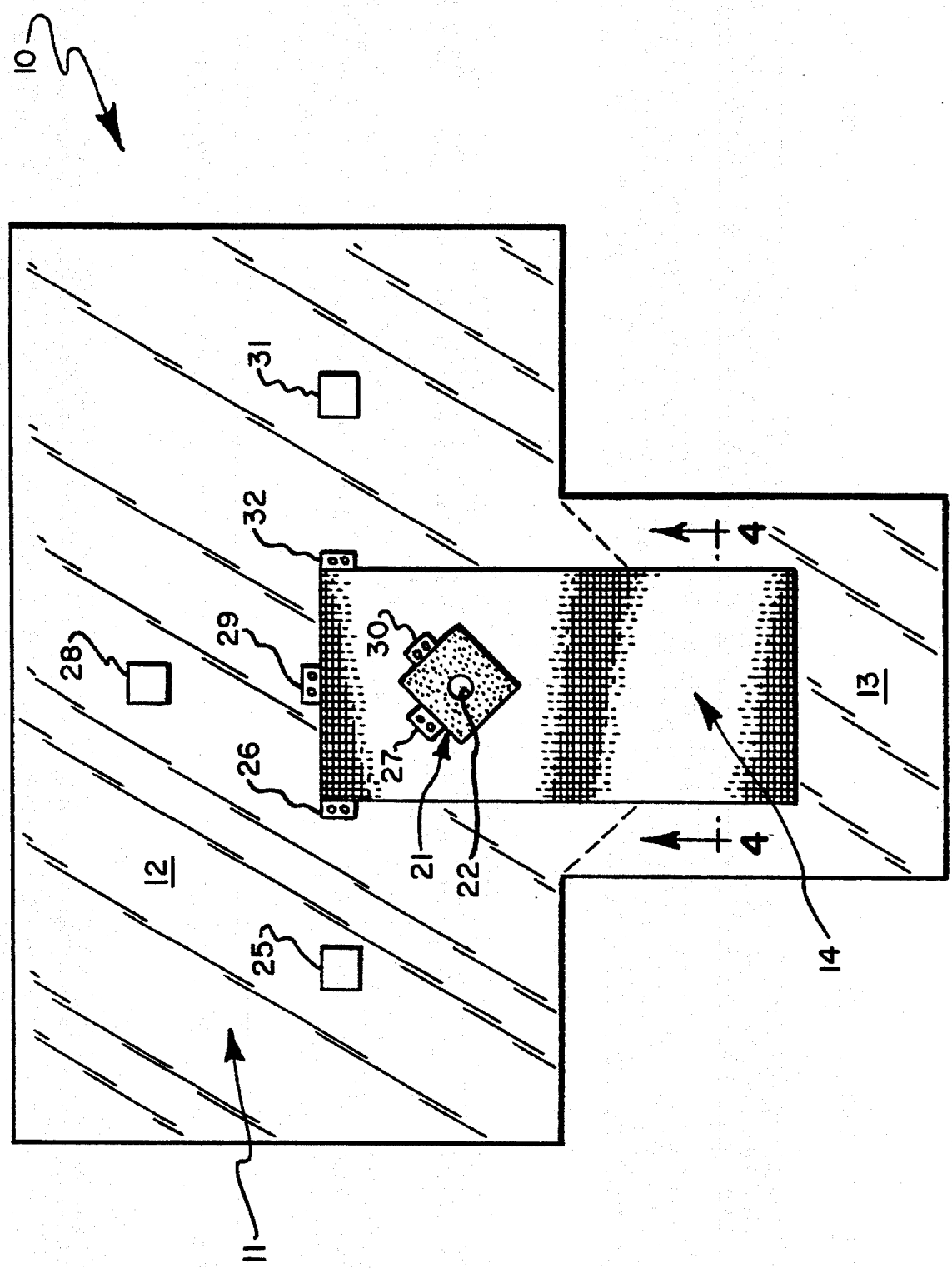
FIG. 1 is a top plan view of the preferred embodiment of the drape.

At the outset, it should be clearly understood that like reference numerals are intended to identify the same structural elements, portions or surfaces consistently throughout the several drawings figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Adverting to FIG. 1, the present invention, drape 10 is shown. It generally comprises a base sheet 11 having a main area 12, an extension area 13, a work surface 14, and a dam 21. A base sheet 11 is made of polypropylene, a material well-known to be suitable for surgical drapes because it is inexpensive and relatively strong. It is desirable to have drape 10 be inexpensive because it can only be used once and then must be properly disposed.

Figure 2:
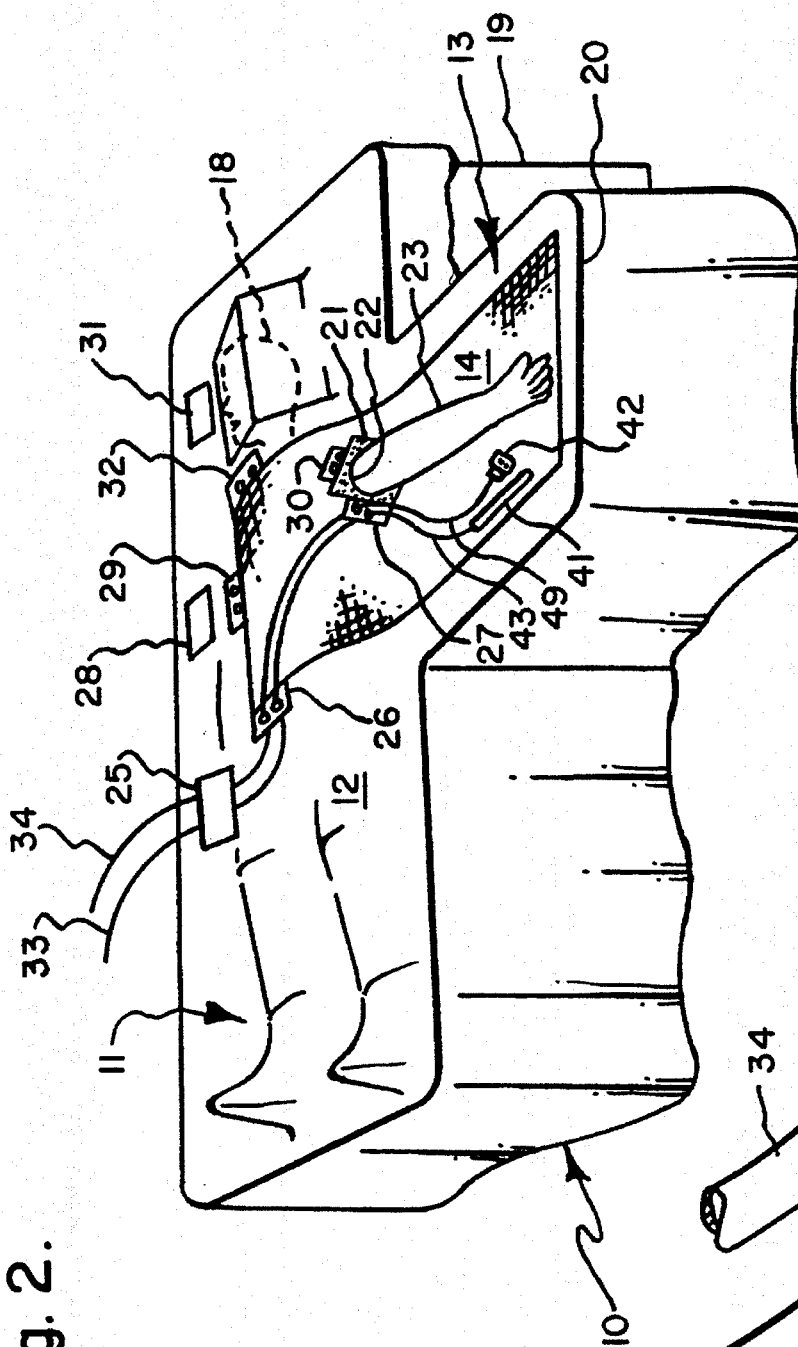
FIG. 2 is a perspective view of the drape as used during arm/hand surgery.

Adverting to FIG. 2, drape 10 is shown during arm/hand surgery. Arm/hand surgery is often performed using a surgical table 19 having an extension 20 where the subject extremity 23 lies. Patient 18 lies on surgical table 19 covered by main area 12 with subject extremity 23 passing through adjustable opening 22. The general T-shape of drape 10 accommodates this typical arm/hand surgery. Further, drape 10 is symmetric, allowing surgery on either arm by merely repositioning drape 10.

Although leg/foot surgery does not utilize extension 20 like arm/hand surgery, drape 10 can still accommodate leg/foot surgery, FIG. 3 shows how drape 10 is positioned for leg/foot surgery. Patient 18 lies on surgical table 19 covered by main area 12 with his fight leg 24 placed through adjustable opening 22 and resting on surgical table 19.

Adverting to FIG. 2, and 3, drape 10 is larger than surgical table 19 or surgical table 19 and extension 20 combined. No matter in what position patient 18 lies, drape 10 will fall over the edges of surgical table 19 and extension 20. This helps maintain the sterile environment under drape 10.

Adverting to FIG. 1, a rectangular work surface 14 is attached to drape 10 partially over main area 12 and partially over extension area 13. Adverting to FIG. 2, the subject extremity 23 always rests on work surface 14 during surgery. Work surface 14 has three layers, each performing a specific function. Adverting to FIG. 4, a cross-section of work surface 14 is shown. During an operation the surgical team will place needed instruments near the subject extremity 23. The constant placing and removal of sharp instruments from drape 10 may cause tearing of drape 10.

Also, the surgical team has a greater chance of accidently penetrating drape 10 with a sharp instrument in the area immediately surrounding subject extremity 23. Moreover, because the surface near subject extremity 23 may not be flat, and the patient does not always lie still during an operation, the instruments may slide when placed near subject extremity 23. Accordingly, upper layer 15 is made of a non-skid, tear resistant material such as polypropylene. Here, a layer of polypropylene substantially thicker than base sheet 11 is used for upper layer 15. Further, upper layer 15 has a quilted texture to prevent sliding.

The entire drape 10 need not be non-skid with superior tear resistant capabilities, only the area where a majority of the action involving surgical instruments occurs. Selective use of reinforcing material reduces the over-all cost of the drape.

Continuing to advert to FIG. 4, absorbent middle layer 16 is impregnated with an antimicrobial compound such as chlorhexidine. Blood and other body fluids along with liquid by-products of surgery often spill onto the area around a surgical procedure. In all instances, these fluids are potentially contaminated or infectious. To prevent the spread of these liquids throughout drape 10, middle layer 16 immobilizes fluids spilled on work surface 14 while its antimicrobial capability decreases the infectious potential of the fluids absorbed.

A bottom layer 17 is liquid impermeable allowing middle layer 16 the opportunity to absorb the volume of a spill without the fluid spreading to base sheet 11. Bottom layer 17 also prevents the liquids absorbed by middle layer 16 from migrating through middle layer 16 over time and into base sheet 11. Bottom layer 17 here is made of a thin plastic.

Adverting to FIGS. 1 and 2, subject extremity 23 is placed through adjustable opening 22 in drape 10. Adjustable opening 22 is adjustable in size because it is defined by dam 21 made of elastomeric material. Here, the elastomeric material is 0.005 inch thick rubber. Because dam 21 is made of elastomeric material, when subject extremity 23 is placed through adjustable opening 22, the elastomeric material will deform, enlarging adjustable opening 22, but dam 21 will maintain a tight engagement with subject extremity 23. The tight engagement protects the sterile environment under drape 10 by preventing migration of infectious materials through work surface 14 at adjustable opening 22.

Similar dams are currently used on drapes. No prior art dam, however, is capable of use on the extremities of all patients ranging from infants to adults. Many times extremity surgery is conducted on infants to correct congenital birth defects. Prior art dams provide adjustable openings with large at rest diameters unable to maintain a tight engagement with an infant's small extremities. This forces surgical teams to contrive solutions such as wrapping the drape around the extremity, but these solutions prove less effective than an elastomeric dam maintaining a tight engagement.

Adverting to FIG. 1, dam 21 is generally square. It is placed on work surface 14 close to the center of main area 12. The patient 18 is always under the center of main area 12. Any portion of any extremity passing through the adjustable opening 22 will rest completely on work surface 14. As mentioned earlier, it is important to have subject extremity 23 on work surface 14 to reduce the chances of tearing drape 10.

A substantial amount of work surface 14 is above dam 21 towards the center of main area 12. Prior art drapes provided a small work surface above their dams. The absence of a larger area prevents effective surgery on an extremity near adjustable opening 23. When using a drape having a smaller area above its dam, it is likely the surgical team will drop an instrument on base sheet 11 and not work surface 14. This may lead to compromising the sterile environment under drape 10. Further, the small work area reduces the total area for the surgical team to conveniently place instruments when not in use. In the present invention work surface 14 is at least one foot beyond the top of dam 21.

Adverting to FIGS. 1 and 2, dam 21 is oriented with its longest internal distance generally parallel with the longitudinal access of work surface 14. This orientation allows the greatest expansion of adjustable opening 22 generally along the length of subject extremity 23. Maximum flexibility in the direction of subject extremity 23 is important because many extremity operations near the body trunk, and therefore near adjustable opening 22, involve work on joints connecting the body trunk and extremity (e.g., hip to leg and shoulder to arm). For example, not only can subject extremity 23, an arm, pass through adjustable opening 22, but the opening can be extended along the longest internal distance of dam 21 to expose the shoulder of patient 18. This flexibility along the length of the subject extremity 23 ensures a joint can be partially exposed without expanding adjustable opening 22 by cutting dam 21, thereby destroying the tight engagement.

The invention also provides unique cord stays to restrain the movement of cords utilized in surgery. Many surgical procedures today use instruments having cords. These cords provide power, drop hydraulic pressure, fiberoptic lines, suction and other capabilities to devices such as pneumatic power drills, fiberoptic scopes and electro cautery. Unfortunately, cords often shift from their desired location and interfere with an operation or contaminate the surgical area. Medical personnel have recognized the importance of restricting the movement of cords and solve the problem by clamping cords directly to a surgical drape. This solution is unacceptable because the weight and sharpness of a clamp many times causes a tear in the drape, breaching the sterile environment under the drape. The present invention provides a series of cord stays 25–32 attached to drape 10 for immobilizing cords.

Adverting to FIG. 2, patient 18 is shown prepared for extremity surgery using drape 10. Extremity 23 breaches drape 10 at adjustable opening 22 and lies on work surface 14. Cords 33 and 34 originate at equipment in the operating room not shown. They proceed over patient 18 and then are first immobilized by stay 25. Adverting to FIG. 5, stay 25 is a strip of flexible material attached at its center 35 to drape 10. Stay 25 has two free ends 36 and 37. End 36 has one half of a velcro combination which is a hook and loop connection, on its exterior surface 38. End 37 has the opposite haft of a velcro combination which is a hook and loop connection, on its interior surface 39. End 36 is positioned to overlay cords 33 and 34 as they traverse center 35, and end 37 is positioned so interior surface 39 contacts exterior surface 38 completing a velcro connection, thus, forming a complete loop small enough to immobilize cords 33 and 34.

Figure 6:
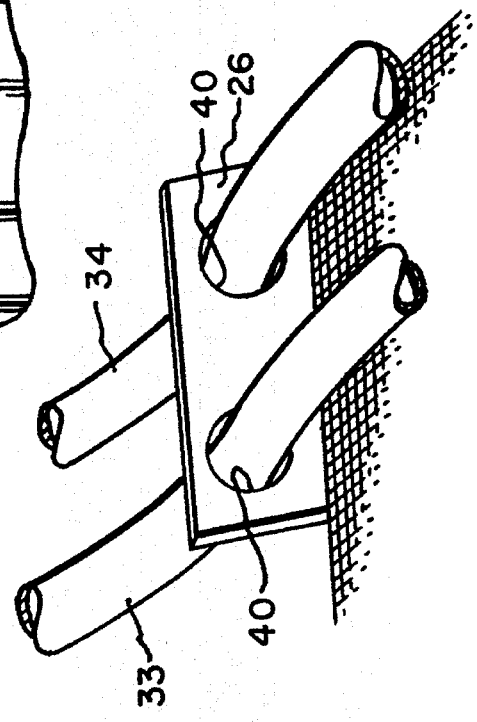
FIG. 6 is a perspective view of a second cord stay.

Adverting to FIGS. 2 and 6, stays 26 and 27 hold cords 33 and 34 differently than stay 25. Stays 26 and 27 are flexible strips of material attached to the edge of work surface 14 and dam 21 respectively. Both stays 26 and 27 have variable openings 40 cords 33 and 34 pass through. Similar to adjustable opening 22 and dam 21, variable opening 40 enlarges to accommodate a cord of dimension greater than its at-rest diameter. This enlargement allows cords 33 and 34 to pass through stays 26 and 27. The enlargement also forms a tight engagement between stay 26 and 27 and cords 33 and 34, thus preventing the free movement of cords 33 and 34.

Adverting to FIG. 2, after passing through stay 27, cords 33 and 34 terminate at instruments 41 and 42. Between stay 27 and instruments 41 and 42 are cord portions 43 and 44 capable of free movement. Cord portions 43 and 44 allow the physician to effectively use instruments 41 and 42. If instrument 41 or 42 is disturbed, they may fall over the edge of extension 20 but will not reach the operating room floor. Further, the portions of cords 33 and 34 engaged by cord stays 25–27 will not roll off patient 18 or roll onto subject extremity 23.

Modifications to the Invention

Although a single embodiment of the invention is disclosed, it is clear from the specification, drawings and description of the invention that many modifications and changes may be made without departing from the invention.

For instance, although two types of cord stays integrated with the drape are disclosed, it is clear other holding devices such as a belt and buckle mechanism, snap and lock, or simple lace ties may be used to immobilize cords.

Too, the shape of the dam does not need to be square. It can be a number of other shapes including round or rectangular.

These and other modifications and changes to the invention would be readily apparent to one of skill in the art and anticipated by the specification and description of the invention, as well as the following claims.

What is claimed is:

1. A universal drape for extremity surgery, comprising:

a base sheet large enough to cover an entire person of any size having a main area and extension area;

a longitudinal work surface having upper and lower portions, and having an upper surface, said upper portion positioned on said main area and said lower portion positioned on said extension area, said upper surface being substantially tear resistant and non-slippery;

a dam of elastomeric material having an adjustable opening, said dam positioned on said work surface upper portion so said distance between said dam and the upper edge of said work surface upper portion is at least twelve inches and any extremity placed through said opening can rest completely on said work surface, said dam oriented with its longest dimension generally parallel to the longitudinal axis of said work surface; and cord stays positioned adjacent the edge of said dam;

whereby a length of a cord near said opening passed through a series of said cord stays is held fast.

2. The device according to claim 1 wherein said cord stays are also positioned adjacent said base sheet.

3. The device according to claim 1 wherein said cord stays are also positioned adjacent the edge of said work surface.

4. A universal drape for extremity surgery, comprising:

a base sheet large enough to cover an entire person of any size having a main area and extension area;

a longitudinal work surface having upper and lower portions, and having an upper surface, said upper portion positioned on said main area and said lower portion positioned on said extension area, said upper surface being substantially tear resistant and non-slippery;

a dam of elastomeric material having an adjustable opening, said dam positioned on said work surface upper portion so said distance between said dam and the upper edge of said work surface upper portion is at least twelve inches and any extremity placed through said opening can rest completely on said work surface, said dam oriented with its longest dimension generally parallel to the longitudinal axis of said work surface; and cord stays positioned adjacent the edge of said work surface and said base sheet;

whereby a length of a cord near said opening passed through a series of said cord stays is held fast.

* * * * *